United States Patent [19]
Shorin et al.

[11] Patent Number: 5,285,556
[45] Date of Patent: Feb. 15, 1994

[54] INTEGRAL POLYMERIC CLAMP

[76] Inventors: Joseph E. Shorin; Peter Sullivan, both of 2245 Industrial Blvd., Sarasota, Fla. 34234

[21] Appl. No.: 990,236
[22] Filed: Dec. 14, 1992
[51] Int. Cl.⁵ .................................................. A44B 1/04
[52] U.S. Cl. ........................................ 24/487; 24/543
[58] Field of Search ............... 24/487, 543, 544, 545, 24/557, 558, 67.9; 251/9, 10

[56]  References Cited
U.S. PATENT DOCUMENTS

| | | | |
|---|---|---|---|
| 235,127 | 5/1875 | Grant | 24/543 X |
| 350,850 | 10/1886 | Tatum . | |
| 3,127,656 | 4/1964 | Schwabe et al. | 24/487 |
| 3,382,549 | 5/1968 | Price | 24/487 |
| 3,461,876 | 8/1969 | Miller . | |
| 3,512,227 | 5/1970 | Krawagna . | |
| 3,518,731 | 7/1970 | Ostrowsky et al. | 24/487 |
| 3,561,077 | 2/1971 | Grant | 24/487 X |
| 3,594,852 | 7/1971 | Krawagna . | |
| 3,612,475 | 10/1971 | Dinger . | |
| 3,713,622 | 1/1973 | Dinger . | |
| 3,766,925 | 10/1973 | Rubricius . | |
| 3,942,228 | 3/1976 | Buckman . | |
| 4,235,412 | 11/1980 | Rath . | |
| 4,247,076 | 1/1981 | Larkin | 24/487 X |
| 4,346,869 | 8/1982 | MacNeill . | |
| 4,453,295 | 6/1984 | Laszczower . | |
| 4,588,160 | 5/1986 | Flynn . | |
| 4,589,626 | 5/1986 | Kurtz . | |
| 4,673,161 | 6/1987 | Flynn . | |
| 4,802,650 | 2/1989 | Stricker . | |
| 5,035,399 | 7/1991 | Rantanen-Lee . | |

FOREIGN PATENT DOCUMENTS

| | | |
|---|---|---|
| 791907 | 8/1968 | Canada . |
| 835010 | 2/1970 | Canada . |
| 840059 | 4/1970 | Canada . |
| 840060 | 4/1970 | Canada . |
| 875956 | 7/1971 | Canada . |
| 2078849 | 1/1982 | United Kingdom ............... 24/487 |

*Primary Examiner*—Laurie K. Cranmer
*Attorney, Agent, or Firm*—Mark T. Basseches; Paula T. Basseches

[57] ABSTRACT

An integral polymeric clamp device is disclosed. The clamp device is comprised of a base portion to which is hingedly connected a two arm clamping assembly actuable from an open position to a closed position wherein a component of a second arm of the assembly clampingly engages a stop surface formed on the base of the assembly. The arms are locked in clamping position when a hinged connection between the arms shifts from a first to a second side of a line extending between the stop surface and the hinged connection of the first arm to the body portion Movement of the clamp member into engagement with the fixed stop portion on the body of the clamp is assured by a locator link hingedly interposed between the body portion and the arm carrying the moving component of the clamp assembly.

12 Claims, 3 Drawing Sheets

INTEGRAL POLYMERIC CLAMP

BACKGROUND OF THE INVENTION

1. Field of the Invention

This invention is directed to a clamp device and more particularly to a integrally molded clamp formed of polymeric material.

Still, more particularly, the invention is directed a ubiquitous polymeric clamp, which is inexpensive to manufacture, durable, and with minor modifications useful in multipurpose applications.

By way of example, the clamp may be employed as a hose clamp, in the manner of the clothespin, wall mounted as a note holder, as a bed sheet clamp, etc.

2. The Prior Art

As is well known, clamp devices such as clothespins and the like are available in a multiplicity of configurations. Many of such devices are of multipart constructions, whereby there are encountered assembly difficulties.

In order to avoid the expense inhering in clamps fabricated of different materials and requiring assembly, it has been proposed to fabricate hinges, clamps and the like, which are integrally molded of polymeric materials, the components of the clamp being connected by so-called "living hinges".

Representative examples of such devices may be found in U.S. Pat. No. 3,720,979 and corresponding Canadian patent 840,059; U.S. Pat. No. 3,594,852 and corresponding Canadian patent 840,060; Canadian patents 791,907; 835,010 and 875,956.

The following U.S. Pat. Nos. were located as a result of a prior art search made in respect of an evaluation of the instant invention: 350,850; 3,461,876; 3,612,475; 3,713,622; 3,942,228; 4,235,412; 4,346,869; 4,453,295; 4,588,160; 4,589,626; 4,673,161; 4,802,650 and 5,035,399.

Of the collected references the following are considered to be of marginal relevance to the instant invention.

U.S. Pat. No. 3,461,876 discloses a clamp having alignment pins to prevent sidewise skewing of the clamp jaws.

U.S. Pat. No. 3,766,925 discloses a clamp having a cam action.

U.S. Pat. Nos. 4,588,160 and 4,673,161 show lateral slots formed in the clamp enabling the clamp to be mounted sidewise over a tube.

SUMMARY OF THE INVENTION

The present invention is directed to a clamp device which is integrally molded from resilient plastic material, illustratively but without limitation of polypropylene. The clamp of the invention is characterized in that it may be readily molded, is inexpensive to fabricate, is integrally formed, is durable, is easy to use, is adapted to clamping various thicknesses of materials, and with minor modifications may be used for a wide variety of purposes.

Briefly stated, the clamp includes a rigid base portion having a stop surface adjacent an end, the stop surface being disposed within a hooklike configuration. A clamp assembly is hingedly connected to the base portion and includes a distal end shiftable toward and away from the stop surface so as to define a clamping area between the stop surface and distal end. The clamp assembly is comprised of two arms hingedly connected. Clamping is effected when the hinged connection between the arms is shifted toward the base from a position outside a line extending between the stop surface and hinge linking the clamp assembly to the base, to the opposite side of said line.

An important feature of the invention resides in the provision of a locator link hingedly connected to the clamp assembly at one end and to the base portion at its other end. The locator link functions to assure that the distal end of the clamp assembly reliably enters into the hooklike configuration as the clamp is closed.

It is accordingly an object of the invention to provide a ubiquitous integrally molded polymeric clamp device which may be readily manufactured, requires no assembly, and is durable and inexpensive to manufacture.

A further object of the invention is the provision of a clamp of the type described which may be integrally molded together with ancillary attachments, such as a backing for wall mounting, a hook for connection to a clothesline or a rubber band, or back to back clamps enabling the attachment of articles to each other.

A still further object of the invention is the provision of a clamp of the type described which is especially suitable for use as a hose clamp.

DETAILED DESCRIPTION OF DRAWINGS

Figure 1:
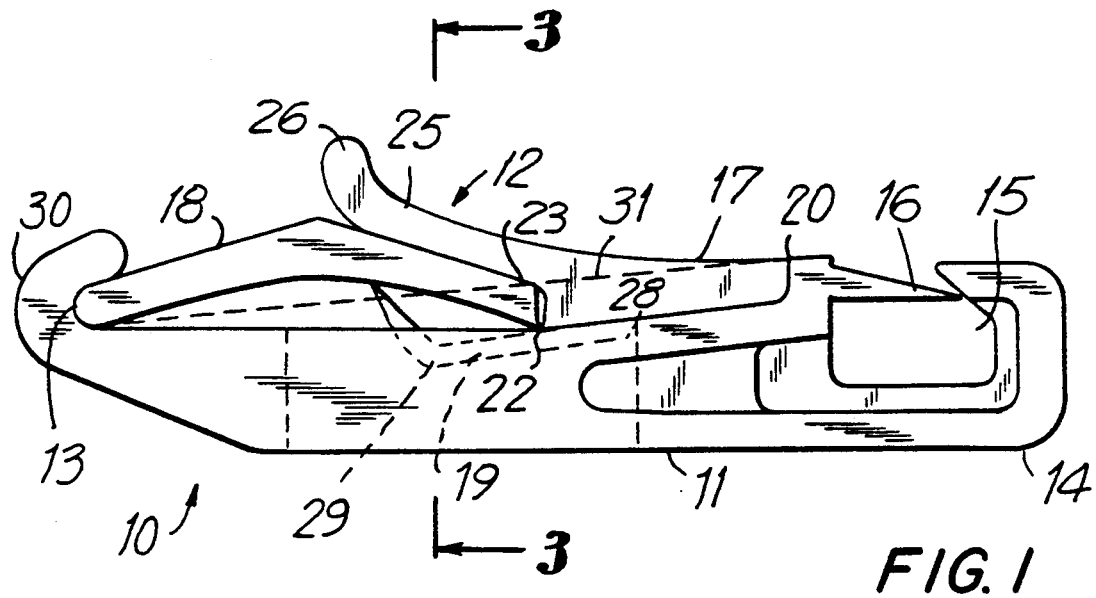
FIG. 1 is a side elevational view of the clamp in the closed position thereof.
Figure 2:
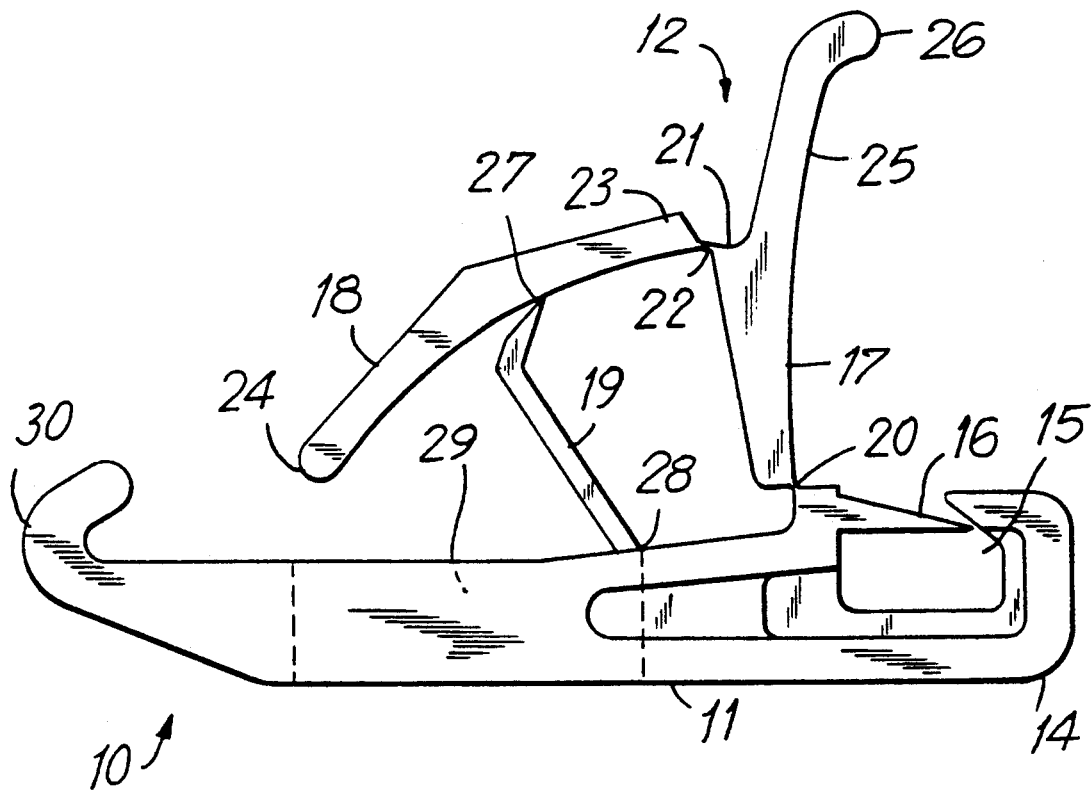
FIG. 2 is a view similar to FIG. 1 showing the position of the clamp parts in the open condition thereof.
Figure 3:
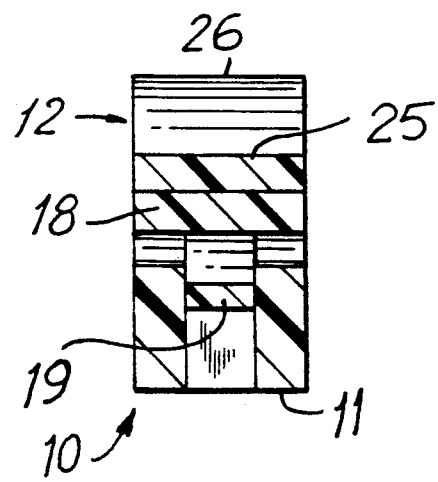
FIG. 3 is a vertical sectional view taken on the line 3—3 of FIG. 1.

Referring to FIGS. 1 through 3 there is disclosed a first embodiment of the invention, specifically a clamp member 10 integrally fabricated of resilient polymeric material, illustratively but without limitation polypropylene. The clamp 10 includes a relatively rigid body or base portion 11, a clamp assembly identified generally by the reference numeral 12, and a stop surface 13. The end 14 of the clamp remote from the stop surface 13 may be formed with any desired configuration depending upon the intended use of the clamp.

By way of illustration, the clamp 10 at end 14 defines an aperture 15 for the reception for example of a cord etc., access to the aperture 15 being facilitated by resilient flap 16 which may be deflected to enable a cord or the like to enter aperture 15. The assembly at the end 14 forms no part of the instant invention and a variety of substitute components may be integrally molded to the end 14. For example, a flat bracket may be employed to permit the clamp to be wall mounted. Similarly, two clamps may be molded back to back.

The clamp assembly 12 forming the principal advance of the instant invention is comprised of a pair of lever arms 17,18 and a locator link 19. Lever 17 is connected by a first hinge 20 to the base portion, the opposite end 21 of lever 17 being connected by hinge 22 to a first end 23 of lever 18. The distal end 24 of lever 18 provides the clamping or locking function in conjunction with the stop surface 13. Hinges 20 and 22 are disposed in parallel relation with each other and with the stop surface 13. A grip portion 25 forms an extension of the lever 17, the grip portion including a raised end 26 to facilitate actuation between the open and clamping conditions illustrated in FIGS. 2 and 1 respectively.

The flexible locator link 19 is hingedly connected at 27 to an undersurface of lever 18, hinge 28 connecting the opposite end of the locator link to the base portion. The base portion is recessed as at 29 immediately adjacent hinge 28 to provide clearance for the flexible locator link 19 in the closed position of the clamp.

The operation of the clamp will be evident from the preceding description. The clamp in the open position shown in FIG. 2 is shifted to the closed position of FIG. 1 by movement of the gripper portion 26 toward the hooklike component 30 surrounding the stop surface 13. An item to be clamped (not shown) is, of course, interposed between stop surface 13 and distal end 24 prior to full closing of the clamp. As the clamp assembly 12 is shifted from the open position of FIG. 2 to the closed position of FIG. 1, it will be observed that the hinge point 22 is shifted from a position above line 31 (FIG. 1) extending between stop surface 13 and hinge point 20 to the opposite side of said line. Since the hinge 22 is below the dead center position represented by line 31 the compressive forces inhering in the resilience of the levers 17 and 18 and augmented by the thickness of the materials clamped tend, in the position of FIG. 1, to urge the hinge member 22 downwardly or toward the base portion 11, whereby the distal end 24 is fixedly retained at a stable position clamping elements interposed between stop surface 13 and end 24.

The flexible locator link 19 performs an important function in the course of shifting movements from the open to the closed position of the clamp. Specifically, in the absence of link 19 the distal end 24 might pass outwardly above the hook configuration 30, whereby no clamping action would be obtained.

Figure 4:
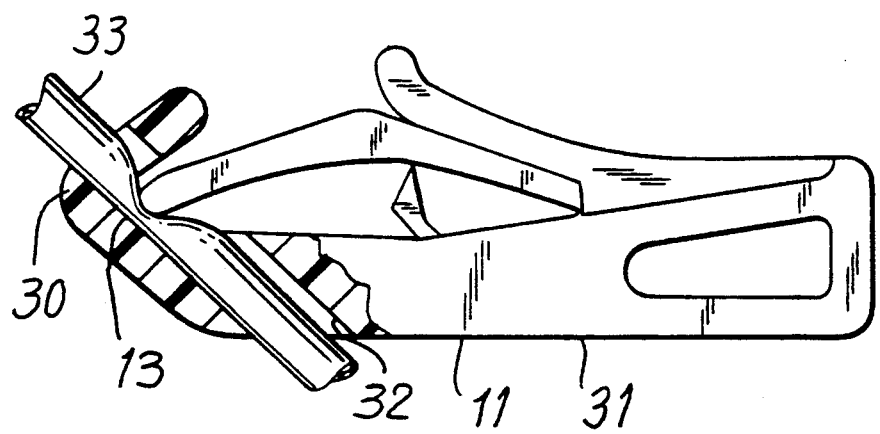
FIG. 4 is a view similar to FIG. 1 illustrating the clamp modified for use as a hose clamp.

Referring now to FIG. 4, there is disclosed a clamp device 31 essentially identical to the device described in connection with FIGS. 1 and 2 with the exception that a bore 32 has been formed through base 11 and the hook configuration 30. The bore 32 lies tangent to the stop surface 13. As will be apparent from FIG. 4, a hose 33 may be threaded through bore 32, flow through the hose being controlled in accordance with whether the clamp is in the open or closed condition.

Figure 5:
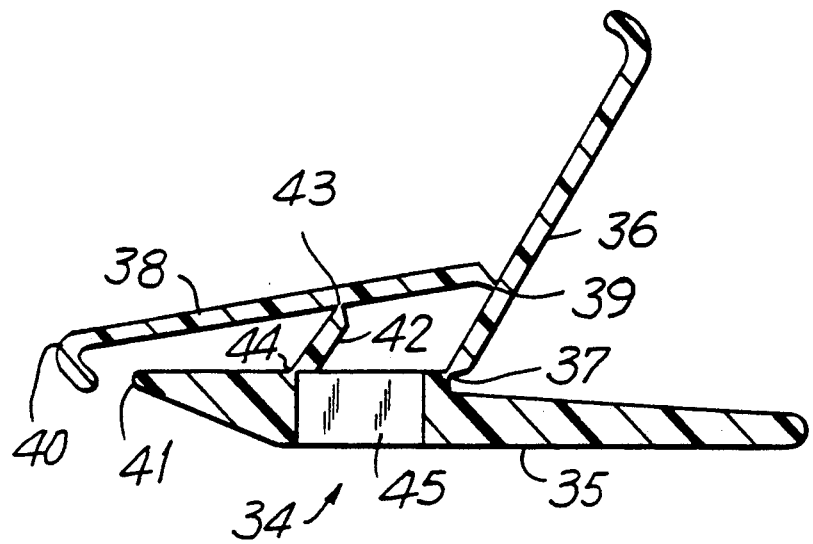
FIGS. 5 and 6 are side elevational views of an embodiment of the invention respectively in the open and closed positions thereof.
Figure 6:
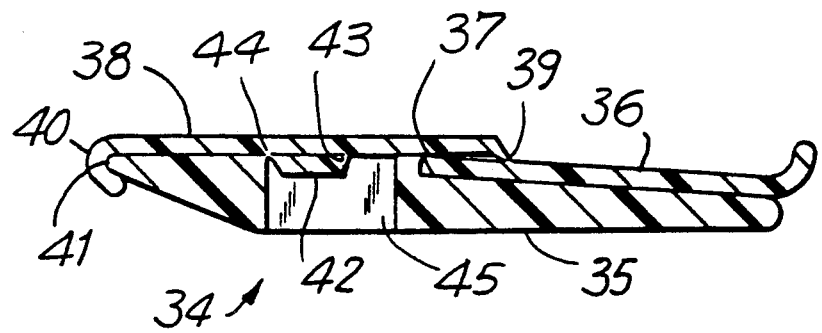

In FIGS. 5 and 6 there is disclosed an embodiment of the invention wherein clamping is effected on an exterior surface of the clamp device referred to generally as 34. Actuator lever 36 is hingedly connected at 37 to the base portion 35, locking lever 38 being linked to lever 36 at living hinge point 39 generally centrally of the lever 36. Lever 38 includes at its distal end a hook configuration 40 which is shiftable toward and away from stop surface 41 at the end of the body portion 35 in accordance with the movement of lever 36.

A flexible locator link member 42 is interposed between lever 38 and body 35 being joined at its ends to the lever and body by living hinges 43 and 44 respectively. As the lever 36 is shifted from the position of FIG. 5 (opened) to the position of FIG. 6 (closed), the hook 40 will be drawn downwardly by link 42 and inwardly toward the stop surface 41 and as hinge 39 of lever 36 reaches past stable dead center position (extension of line between stop 41 and hinge 37), an article interposed between hook 40 and distal end 41 will be clampingly retained between these parts. The link 42, in the clamped position, is disposed within recess 45 formed in the body portion 35.

As will be apparent from the preceding description there is provided in accordance with the invention a new and improved integral polymeric clamp assembly readily adaptable to a multitude of uses. The device is particularly suited for use as a hose clamp, i.e. for thin, walled, rubber or plastic tubing, such as is employed in connection with IV bottles, enema tubes, and the like The uses to which the clamp may be put are virtually endless including inter alia as a means of gripping bed sheets, as a note or memo display when wall mounted, as a clothes pin for mounting on a clothesline, etc.

As will be apparent to those skilled in the art and familiarized with the instant disclosure, numerous variations in details of construction may be made without departing from the spirit of the invention. Accordingly, the invention is to be broadly construed within the scope of the appended claims.

Having thus described the invention and illustrated its use, what is claimed as new and is desired to be secured by Letters Patent is:

1. An integrally molded clamp device of resilient polymeric material comprising a rigid base portion having a stop surface adjacent an end thereof, a clamp assembly moveably connected to said base portion, said clamp assembly including a first lever arm having first and second ends, a first hinge parallel to and spaced from said stop surface linking said first end of said first lever arm to said base portion, a second lever arm having a first end and a distal end, a second hinge member parallel to said first hinge member linking said first end of said second arm with said second end of said first arm, said distal end of said second arm being shifted toward and away from said stop surface responsive to movement of said second hinge toward and away from said base portion, said clamp assembly being locked in stable clamping condition with said distal end yieldably biased toward said stop surface when said second hinge is shifted to a location between said base portion and a line extending between said stop surface and said first hinge.

2. A device in accordance with claim 1 wherein said base portion includes a recess, said locator link being disposed within said recess in said clamping condition of said clamp assembly.

3. A device in accordance with claim 1 wherein said first lever arm includes a grip portion projecting beyond said second end.

4. A device in accordance with claim 4 wherein said grip portion of said first arm overlies and engages said second lever arm in said clamping condition of said clamp assembly.

5. A device in accordance with claim 1 and including a hook configuration on said base portion in encompassing relation of said stop surface, said distal end lying within said hook configuration in said clamping condition of said clamp assembly.

6. A device in accordance with claim 6 and including a bore extending through said base portion and hook configuration adjacent said stop surface whereby a tube threaded through said bore is clamped between said stop surface and distal end in said clamping condition of said clamp assembly.

7. A clamp device in accordance with claim 1 wherein said distal end of second arm includes a hook configuration positioned to lie in encompassing relation of said stop surface in said clamping condition of said clamp assembly.

8. An integrally molded clamp device of resilient polymeric material comprising a rigid base portion having a stop surface adjacent an end thereof, a clamp assembly moveably connected to said base portion, said clamp assembly including a first lever arm having first and second ends, a first hinge parallel to and spaced from said stop surface linking said first end of said first lever arm to said base portion, a second lever arm having a first end and a distal end, a second hinge member parallel to said first hinge member linking said first end of said second arm with said second end of said first arm, the combined length of said first and second arms exceeding the distance between said stop surface and said first hinge, a flexible locator link interposed between said second arm and said base portion, said link having end portions hingedly connected respectively to said base portion and second arm, a recess formed in said base portion in registry with said locator link, said distal end of said second arm being shifted toward and away from said stop surface responsive to movement of said second hinge toward and away from said base portion, said clamp assembly being locked in stable clamping condition with said distal end yieldably biased toward said stop surface when said second hinge is shifted to a location between said base portion and a line extending between said stop surface and said first hinge, said link in said clamping condition being disposed within said recess.

9. A device in accordance with claim 8 wherein said first lever arm includes a grip portion projecting beyond said second end.

10. A device in accordance with claim 9 wherein said grip portion of said first arm overlies and engages said base in said clamping condition of said clamp assembly.

11. A device in accordance with claim 8 and including a hook configuration on said distal end of said second arm, said base portion lying within said hook configuration in said clamping condition of said clamp assembly.

12. A device in accordance with claim 8 and including a bore extending through said base portion and hook configuration adjacent said stop surface whereby a tube threaded through said bore is clamped between said stop surface and distal end in said clamping condition of said clamp assembly.

* * * * *